United States Patent
Huang et al.

(10) Patent No.: US 11,116,837 B2
(45) Date of Patent: Sep. 14, 2021

(54) VACCINE COMPOSITION COMPRISING HEPATITIS B VIRUS LIKE PARTICLE AS ADJUVANT

(71) Applicant: National Taiwan University, Taipei (TW)

(72) Inventors: Limin Huang, Taipei (TW); Jenmin Huang, East District Hsinchu (TW)

(73) Assignee: National Taiwan University, Taipei (TW)

( * ) Notice: Subject to any disclaimer, the term of this patent is extended or adjusted under 35 U.S.C. 154(b) by 63 days.

(21) Appl. No.: 16/463,357

(22) PCT Filed: Nov. 22, 2017

(86) PCT No.: PCT/CN2017/112350
§ 371 (c)(1),
(2) Date: May 22, 2019

(87) PCT Pub. No.: WO2018/095327
PCT Pub. Date: May 31, 2018

(65) Prior Publication Data
US 2019/0290754 A1    Sep. 26, 2019

Related U.S. Application Data

(60) Provisional application No. 62/425,079, filed on Nov. 22, 2016.

(51) Int. Cl.
| | |
|---|---|
| *A61K 39/00* | (2006.01) |
| *A61K 39/12* | (2006.01) |
| *A61K 39/155* | (2006.01) |
| *C07K 14/005* | (2006.01) |
| *C12N 7/00* | (2006.01) |
| *A61K 39/39* | (2006.01) |
| *A61P 31/14* | (2006.01) |
| *C07K 14/02* | (2006.01) |

(52) U.S. Cl.
CPC .............. *A61K 39/39* (2013.01); *A61K 39/12* (2013.01); *A61P 31/14* (2018.01); *C07K 14/02* (2013.01); *C12N 7/00* (2013.01); *A61K 2039/5258* (2013.01); *A61K 2039/541* (2013.01); *A61K 2039/55588* (2013.01); *C12N 2730/10123* (2013.01); *C12N 2760/18534* (2013.01); *Y02A 50/30* (2018.01)

(58) Field of Classification Search
CPC ............ A61K 39/12; A61K 2039/6075; A61K 39/155; C07K 14/005; C12N 2760/18534
See application file for complete search history.

(56) References Cited

U.S. PATENT DOCUMENTS

2016/0324960 A1* 11/2016 Fujinaga ................ A61K 39/02

FOREIGN PATENT DOCUMENTS

| WO | WO2013036973 | * | 3/2013 |
| WO | WO2015048149 | * | 4/2015 |

* cited by examiner

*Primary Examiner* — Barry A Chestnut
(74) *Attorney, Agent, or Firm* — Mintz Levin Cohn Ferris Glovsky and Popeo, P.C.; Peter F. Corless; Joohee Lee

(57) ABSTRACT

The present disclosure provides vaccine compositions and methods for inducing a systemic immune response and a mucosal immune response, wherein the vaccine compositions include an antigen and a hepatitis B core virus-like particle (HBc VLP) as an adjuvant. The vaccine compositions are suitable for administration to the mucosal surface of a subject, and are effective in eliciting a protective immune response against infection.

12 Claims, 12 Drawing Sheets
Specification includes a Sequence Listing.

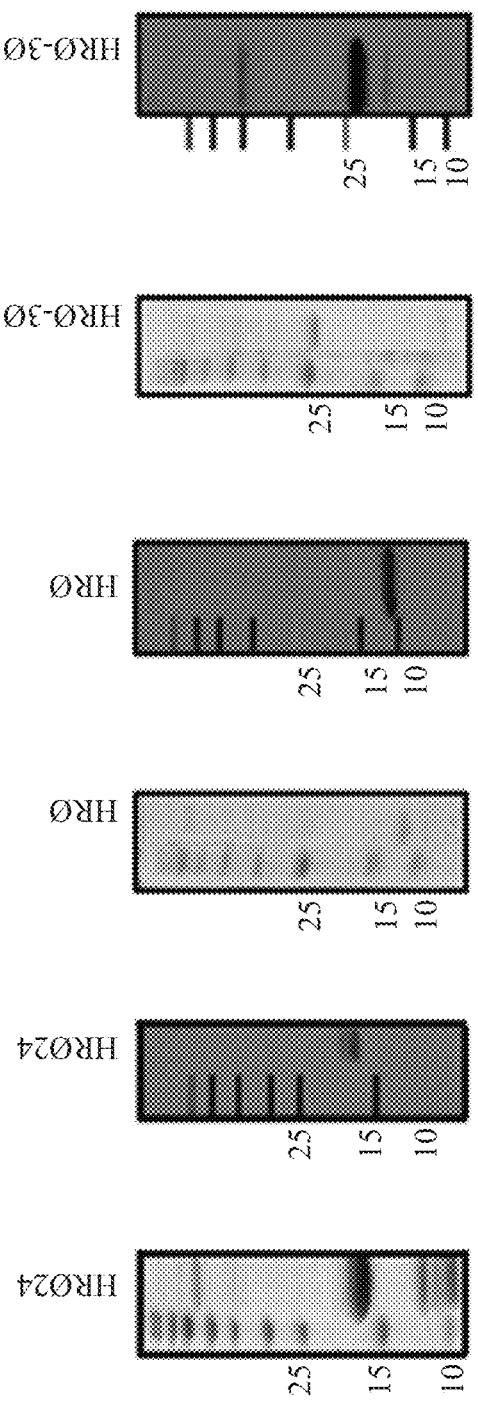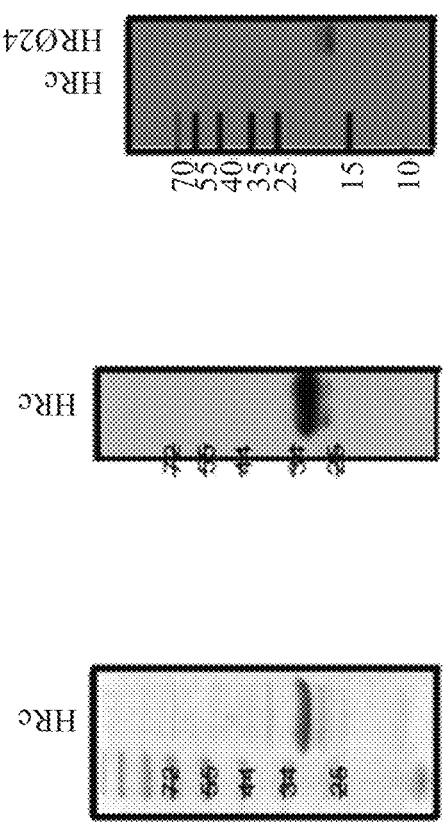

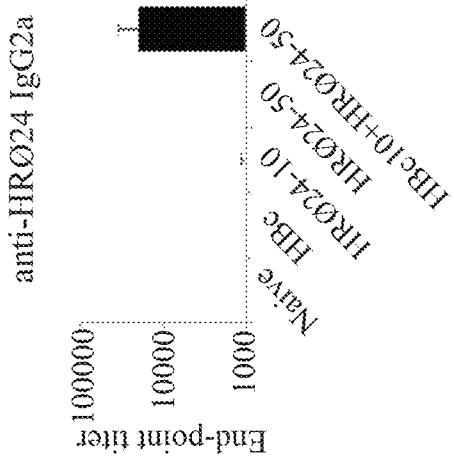
FIG. 4A  FIG. 4B  FIG. 4C
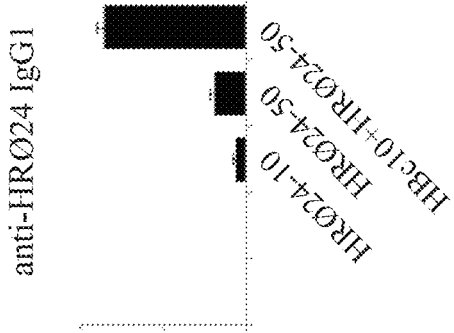
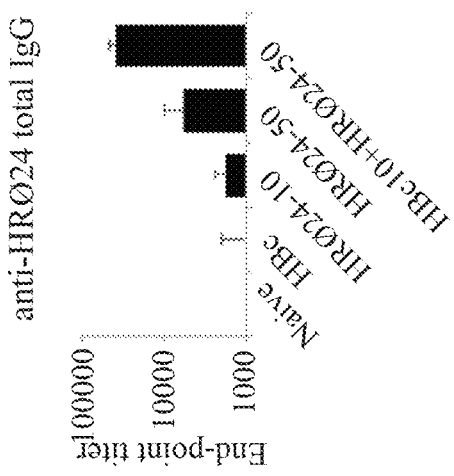
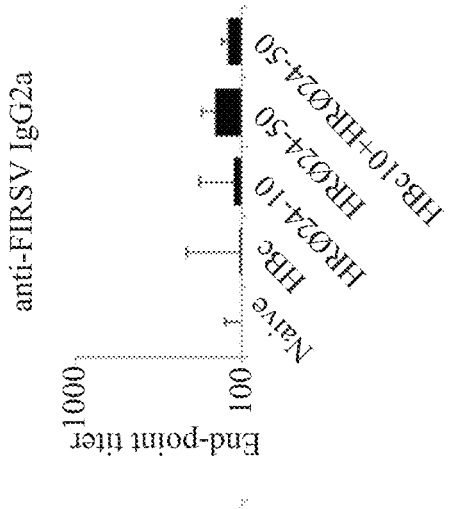
FIG. 4D  FIG. 4E  FIG. 4F
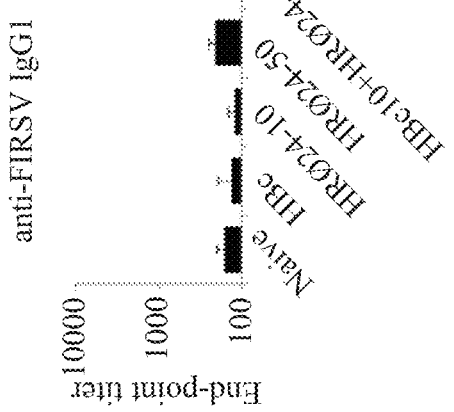
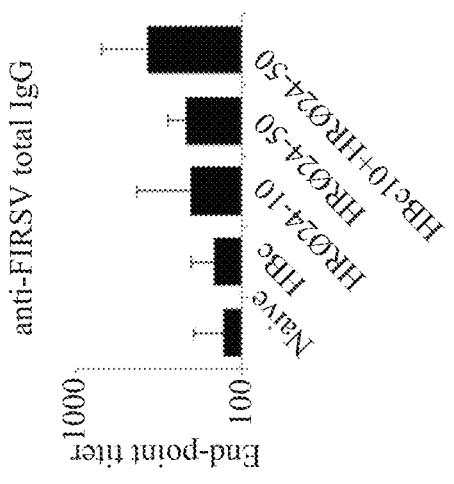

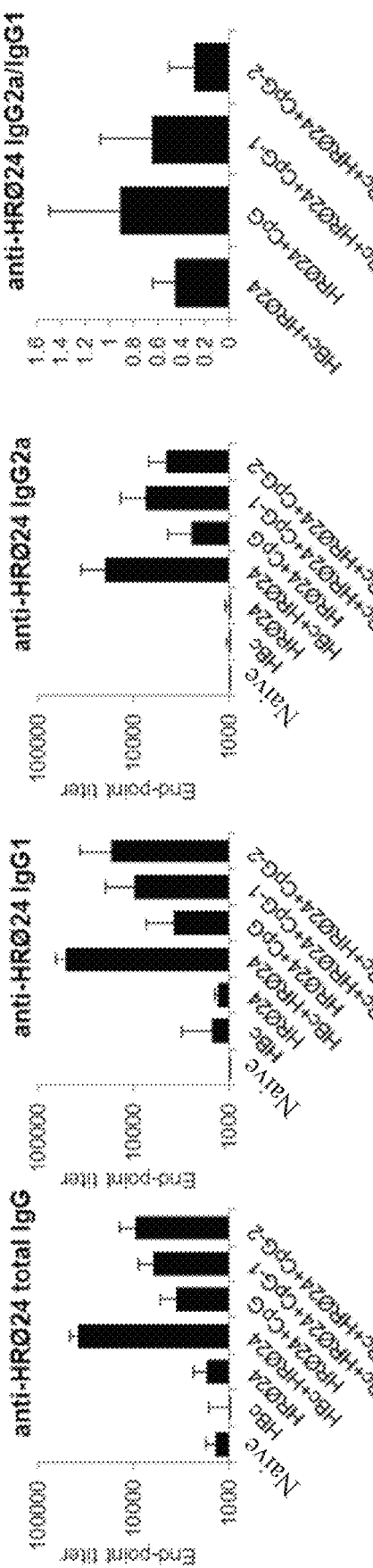
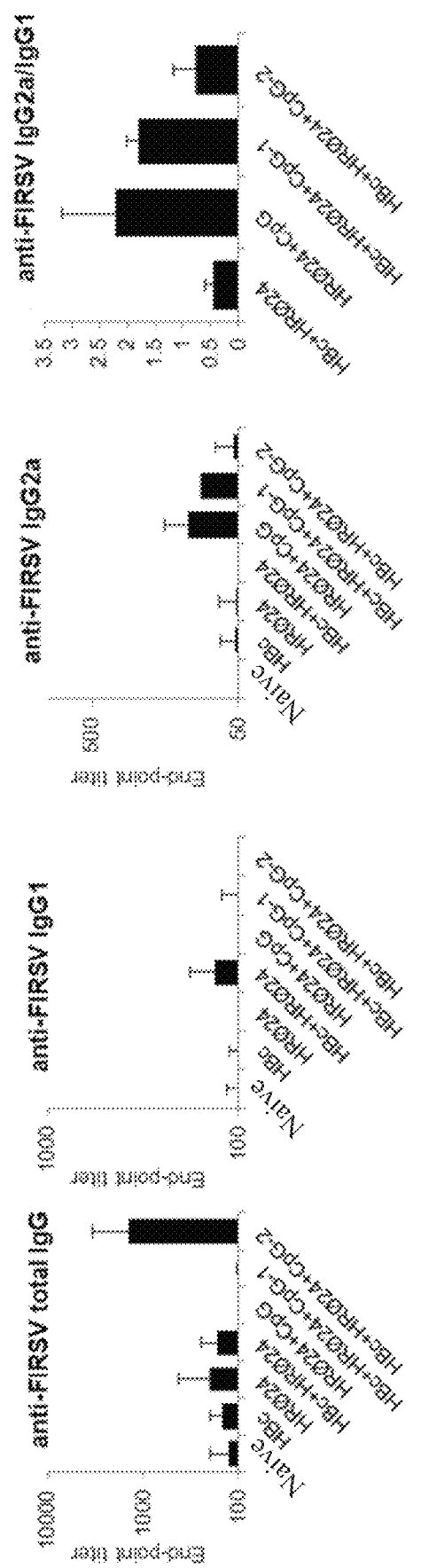

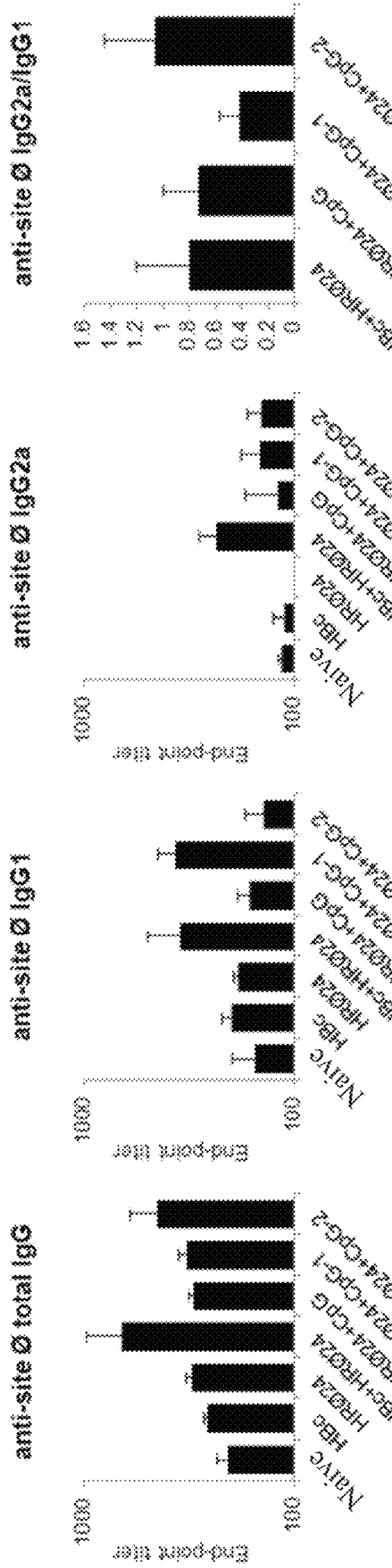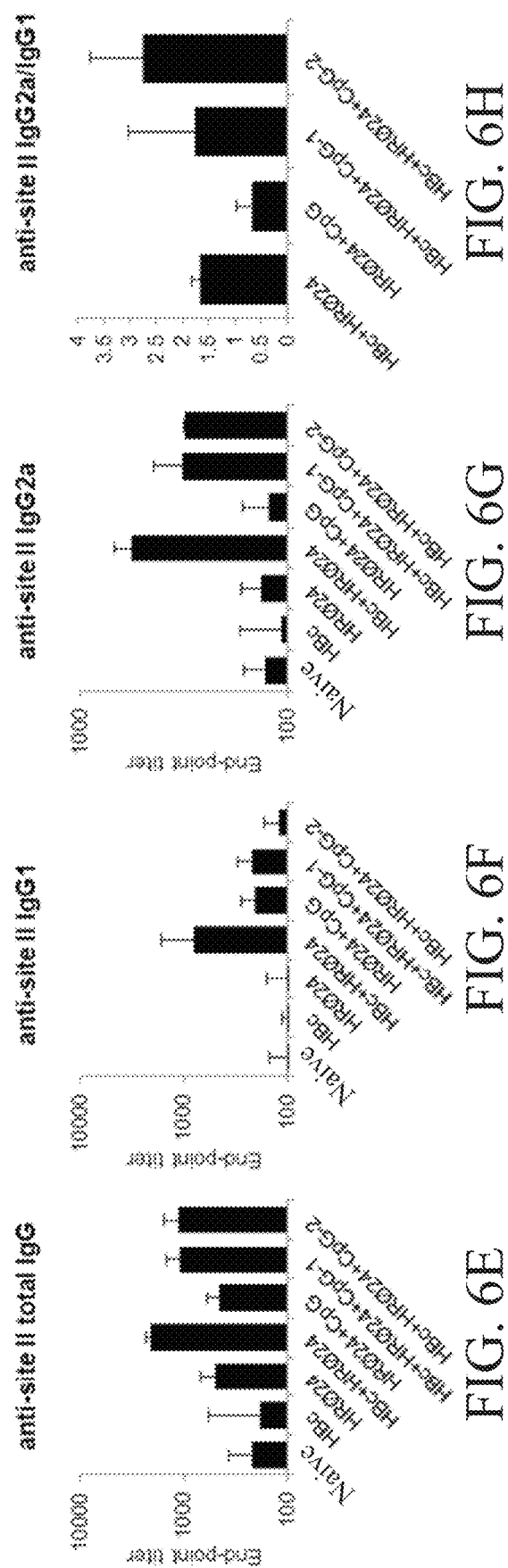

SEQUENCE LISTING

```
<160> NUMBER OF SEQ ID NOS: 30

<210> SEQ ID NO 1
<211> LENGTH: 148
<212> TYPE: PRT
<213> ORGANISM: Hepatitis B virus

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val
145

<210> SEQ ID NO 2
<211> LENGTH: 119
<212> TYPE: PRT
<213> ORGANISM: Artificial Sequence
<220> FEATURE:
<223> OTHER INFORMATION: recombinant RSV F protein HRO

<400> SEQUENCE: 2

Met Ala Val Ser Lys Val Leu His Leu Glu Gly Glu Val Asn Lys Ile
1               5                   10                  15

Lys Ser Ala Leu Leu Ser Thr Asn Lys Ala Val Val Ser Leu Ser Asn
                20                  25                  30

Gly Val Ser Val Leu Thr Ser Lys Val Leu Asp Leu Lys Asn Tyr Ile
```

```
                35                  40                  45
Asp Lys Gln Leu Leu Pro Ile Val Asn Lys Gln Ser Gly Ser Gly Ser
    50                  55                  60

Gly Ser Glu Phe Gly Gly Ser Gly Asn Phe Tyr Asp Pro Leu Val Phe
65                  70                  75                  80

Pro Ser Asp Glu Phe Asp Ala Ser Ile Ser Gln Val Asn Glu Lys Ile
                85                  90                  95

Asn Gln Ser Leu Ala Phe Ile Arg Lys Ser Asp Glu Leu Leu His Asn
            100                 105                 110

Val Asn Ala Gly Lys Leu Glu
        115

<210> SEQ ID NO 3
<211> LENGTH: 202
<212> TYPE: PRT
<213> ORGANISM: Artificial Sequence
<220> FEATURE:
<223> OTHER INFORMATION: recombinant RSV F protein HRO-30

<400> SEQUENCE: 3

Met Ala Val Ser Lys Val Leu His Leu Glu Gly Glu Val Asn Lys Ile
1               5                   10                  15

Lys Ser Ala Leu Leu Ser Thr Asn Lys Ala Val Val Ser Leu Ser Asn
            20                  25                  30

Gly Val Ser Val Leu Thr Ser Lys Val Leu Asp Leu Lys Asn Tyr Ile
        35                  40                  45

Asp Lys Gln Leu Leu Pro Ile Val Asn Lys Gln Ser Gly Ser Gly Ser
    50                  55                  60

Ala Ser Ser Asn Ile Lys Glu Asn Lys Cys Asn Ala Ala Lys Asn Tyr
65                  70                  75                  80

Ile Asp Lys Gln Leu Leu Pro Ile Val Asn Lys Gly Gly Ser Gly Ser
                85                  90                  95

Asn Ile Lys Glu Asn Lys Cys Asn Ala Ala Lys Asn Tyr Ile Asp Lys
            100                 105                 110

Gln Leu Leu Pro Ile Val Asn Lys Gly Gly Glu Phe Ser Asn Ile Lys
            115                 120                 125

Glu Asn Lys Cys Asn Ala Ala Lys Asn Tyr Ile Asp Lys Gln Leu Leu
            130                 135                 140

Pro Ile Val Asn Lys Lys Leu Gly Gly Ser Gly Asn Phe Tyr Asp Pro
145                 150                 155                 160

Leu Val Phe Pro Ser Asp Glu Phe Asp Ala Ser Ile Ser Gln Val Asn
                165                 170                 175

Glu Lys Ile Asn Gln Ser Leu Ala Phe Ile Arg Lys Ser Asp Glu Leu
            180                 185                 190

Leu His Asn Val Asn Ala Gly Lys Leu Glu
            195                 200

<210> SEQ ID NO 4
<211> LENGTH: 164
<212> TYPE: PRT
<213> ORGANISM: Artificial Sequence
<220> FEATURE:
<223> OTHER INFORMATION: recombinant RSV F protein HRO24

<400> SEQUENCE: 4

Met Ala Val Ser Lys Val Leu His Leu Glu Gly Glu Val Asn Lys Ile
1               5                   10                  15
```

-continued

```
Lys Ser Ala Leu Leu Ser Thr Asn Lys Ala Val Val Ser Leu Ser Asn
            20                  25                  30

Gly Val Ser Val Leu Thr Ser Lys Val Leu Asp Leu Lys Asn Tyr Ile
        35                  40                  45

Asp Lys Gln Leu Leu Pro Ile Val Asn Lys Gln Ser Gly Ser Gly Ser
    50                  55                  60

Asn Ser Glu Leu Leu Ser Leu Ile Asn Asp Met Pro Ile Thr Asn Asp
65                  70                  75                  80

Gln Lys Lys Leu Met Ser Asn Asn Val Gln Ile Val Arg Gln Gly Gly
                85                  90                  95

Gly Ser Cys Thr Ala Ser Asn Lys Asn Arg Gly Ile Ile Lys Thr Phe
            100                 105                 110

Ser Asn Gly Gly Gly Ser Gly Asn Phe Tyr Asp Pro Leu Val Phe Pro
        115                 120                 125

Ser Asp Glu Phe Asp Ala Ser Ile Ser Gln Val Asn Glu Lys Ile Asn
    130                 135                 140

Gln Ser Leu Ala Phe Ile Arg Lys Ser Asp Glu Leu Leu His Asn Val
145                 150                 155                 160

Asn Ala Gly Lys

<210> SEQ ID NO 5
<211> LENGTH: 444
<212> TYPE: DNA
<213> ORGANISM: Hepatitis B virus

<400> SEQUENCE: 5
atggacattg acccttataa agaatttgga gctactgtgg agttactctc gtttttgcct      60
tctgacttct ttccttccgt cagagatctt ctagacaccg cctcagctct gtatcgagaa     120
gccttagagt ctcctgagca ttgctcacct caccatactg cactcaggca agccattctc     180
tgctgggggg aattgatgac tctagctacc tgggtgggta ataatttgga agatccagca     240
tccagggatc tagtagtcaa ttatgttaat actaacatgg gtttaaagat caggcaacta     300
ttgtggtttc atatatcttg ccttactttt ggaagagaga ctgtacttga atatttggtc     360
tctttcggag tgtggattcg cactcctcca gcctatagac caccaaatgc ccctatctta     420
tcaacacttc cggaaactac tgtt                                            444

<210> SEQ ID NO 6
<211> LENGTH: 177
<212> TYPE: DNA
<213> ORGANISM: respiratory syncytial virus

<400> SEQUENCE: 6
gccgtgtcta aggtgctgca cctggaggga gaggtgaaca agatcaagag cgccctgctg      60
agcaccaata aggccgtggt gagcctgagc aatggcgtga gcgtgctgac aagcaaggtg     120
ctggacctca agaactacat cgacaagcag ctgctgccca tcgtgaacaa gcagagc        177

<210> SEQ ID NO 7
<211> LENGTH: 90
<212> TYPE: DNA
<213> ORGANISM: respiratory syncytial virus

<400> SEQUENCE: 7
aacagcgagc tgctgagcct gatcaacgac atgcccatca ccaacgacca gaagaagctg      60
atgtccaaca acgtgcagat cgtgcggcag                                       90
```

```
<210> SEQ ID NO 8
<211> LENGTH: 51
<212> TYPE: DNA
<213> ORGANISM: respiratory syncytial virus

<400> SEQUENCE: 8
tgcaccgcca gcaacaagaa ccgcggcatc atcaagacct tcagcaacgg c         51

<210> SEQ ID NO 9
<211> LENGTH: 135
<212> TYPE: DNA
<213> ORGANISM: respiratory syncytial virus

<400> SEQUENCE: 9
aacttctacg accccctggt gttccctagc gacgagttcg atgccagcat cagccaggtg   60
aacgagaaga tcaaccagag cctggccttc atcaggaaga gcgacgagct gctgcacaat  120
gtgaacgccg gcaag                                                   135

<210> SEQ ID NO 10
<211> LENGTH: 27
<212> TYPE: DNA
<213> ORGANISM: Artificial Sequence
<220> FEATURE:
<223> OTHER INFORMATION: HRN-NcoI-F
<220> FEATURE:
<221> NAME/KEY: primer_bind
<222> LOCATION: (1)..(27)

<400> SEQUENCE: 10
ccgccatggc cgtgtctaag gtgctgc                                       27

<210> SEQ ID NO 11
<211> LENGTH: 29
<212> TYPE: DNA
<213> ORGANISM: Artificial Sequence
<220> FEATURE:
<223> OTHER INFORMATION: HRC-XhoI-R
<220> FEATURE:
<221> NAME/KEY: primer_bind
<222> LOCATION: (1)..(29)

<400> SEQUENCE: 11
catgctcgag cttgccggcg ttcacattg                                     29

<210> SEQ ID NO 12
<211> LENGTH: 48
<212> TYPE: DNA
<213> ORGANISM: Artificial Sequence
<220> FEATURE:
<223> OTHER INFORMATION: HRN-A1-F
<220> FEATURE:
<221> NAME/KEY: primer_bind
<222> LOCATION: (1)..(48)

<400> SEQUENCE: 12
catcgtgaac aagcagagcg gttctggttc taacagcgag ctgctgag               48

<210> SEQ ID NO 13
<211> LENGTH: 48
<212> TYPE: DNA
<213> ORGANISM: Artificial Sequence
<220> FEATURE:
<223> OTHER INFORMATION: HRN-A1-R
<220> FEATURE:
<221> NAME/KEY: primer_bind
<222> LOCATION: (1)..(48)
```

<400> SEQUENCE: 13
ctcagcagct cgctgttaga accagaaccg ctctgcttgt tcacgatg                48

<210> SEQ ID NO 14
<211> LENGTH: 43
<212> TYPE: DNA
<213> ORGANISM: Artificial Sequence
<220> FEATURE:
<223> OTHER INFORMATION: A1-A2-F
<220> FEATURE:
<221> NAME/KEY: primer_bind
<222> LOCATION: (1)..(43)

<400> SEQUENCE: 14
gcagatcgtg cggcagggtg gtggttcttg caccgccagc aac                    43

<210> SEQ ID NO 15
<211> LENGTH: 43
<212> TYPE: DNA
<213> ORGANISM: Artificial Sequence
<220> FEATURE:
<223> OTHER INFORMATION: A1-A2-R
<220> FEATURE:
<221> NAME/KEY: primer_bind
<222> LOCATION: (1)..(43)

<400> SEQUENCE: 15
gttgctggcg gtgcaagaac caccaccctg ccgcacgatc tgc                    43

<210> SEQ ID NO 16
<211> LENGTH: 48
<212> TYPE: DNA
<213> ORGANISM: Artificial Sequence
<220> FEATURE:
<223> OTHER INFORMATION: A2-HRC-F
<220> FEATURE:
<221> NAME/KEY: primer_bind
<222> LOCATION: (1)..(48)

<400> SEQUENCE: 16
agaccttcag caacggcggt ggttctggta acttctacga ccccctgg               48

<210> SEQ ID NO 17
<211> LENGTH: 48
<212> TYPE: DNA
<213> ORGANISM: Artificial Sequence
<220> FEATURE:
<223> OTHER INFORMATION: A2-HRC-R
<220> FEATURE:
<221> NAME/KEY: primer_bind
<222> LOCATION: (1)..(48)

<400> SEQUENCE: 17 ccaggggtc gtagaagtta ccagaaccac cgccgttgct gaaggtct                48

<210> SEQ ID NO 18
<211> LENGTH: 59
<212> TYPE: DNA
<213> ORGANISM: Artificial Sequence
<220> FEATURE:
<223> OTHER INFORMATION: Site0-N-F
<220> FEATURE:
<221> NAME/KEY: primer_bind
<222> LOCATION: (1)..(59)

<400> SEQUENCE: 18
gccggatcca gcaacatcaa ggagaacaag tgcaacgccg ccaagaacta catcgacaa   59

<210> SEQ ID NO 19
<211> LENGTH: 60
<212> TYPE: DNA
<213> ORGANISM: Artificial Sequence
<220> FEATURE:
<223> OTHER INFORMATION: SiteO-C-R
<220> FEATURE:
<221> NAME/KEY: primer_bind
<222> LOCATION: (1)..(60)

<400> SEQUENCE: 19
gccaagcttc ttgttcacga tgggcagcag ctgcttgtcg atgtagttct tggcggcgtt    60

<210> SEQ ID NO 20
<211> LENGTH: 31
<212> TYPE: DNA
<213> ORGANISM: Artificial Sequence
<220> FEATURE:
<223> OTHER INFORMATION: HRN-BamHI-R
<220> FEATURE:
<221> NAME/KEY: primer_bind
<222> LOCATION: (1)..(31)

<400> SEQUENCE: 20
gccggatcca gaaccagaac cgctctgctt g                                   31

<210> SEQ ID NO 21
<211> LENGTH: 32
<212> TYPE: DNA
<213> ORGANISM: Artificial Sequence
<220> FEATURE:
<223> OTHER INFORMATION: HRC-EcoRI-F
<220> FEATURE:
<221> NAME/KEY: primer_bind
<222> LOCATION: (1)..(32)

<400> SEQUENCE: 21
cggaattcgg tggttctggt aacttctacg ac                                  32

<210> SEQ ID NO 22
<211> LENGTH: 27
<212> TYPE: DNA
<213> ORGANISM: Artificial Sequence
<220> FEATURE:
<223> OTHER INFORMATION: SiteO-NheI-F
<220> FEATURE:
<221> NAME/KEY: primer_bind
<222> LOCATION: (1)..(27)

<400> SEQUENCE: 22
ctagctagca gcaacatcaa ggagaac                                        27

<210> SEQ ID NO 23
<211> LENGTH: 34
<212> TYPE: DNA
<213> ORGANISM: Artificial Sequence
<220> FEATURE:
<223> OTHER INFORMATION: SiteO-BamHI-R
<220> FEATURE:
<221> NAME/KEY: primer_bind
<222> LOCATION: (1)..(34)

<400> SEQUENCE: 23
gccggatccg cctcccttgt tcacgatggg cagc                                34

<210> SEQ ID NO 24
<211> LENGTH: 27

```
<212> TYPE: DNA
<213> ORGANISM: Artificial Sequence
<220> FEATURE:
<223> OTHER INFORMATION: SiteO-BamHI-F
<220> FEATURE:
<221> NAME/KEY: primer_bind
<222> LOCATION: (1)..(27)

<400> SEQUENCE: 24
gccggatcca gcaacatcaa ggagaac                                    27

<210> SEQ ID NO 25
<211> LENGTH: 33
<212> TYPE: DNA
<213> ORGANISM: Artificial Sequence
<220> FEATURE:
<223> OTHER INFORMATION: SiteO-EcoRI-R
<220> FEATURE:
<221> NAME/KEY: primer_bind
<222> LOCATION: (1)..(33)

<400> SEQUENCE: 25
cggaattcgc ctcccttgtt cacgatgggc agc                             33

<210> SEQ ID NO 26
<211> LENGTH: 26
<212> TYPE: DNA
<213> ORGANISM: Artificial Sequence
<220> FEATURE:
<223> OTHER INFORMATION: SiteO-EcoRI-F
<220> FEATURE:
<221> NAME/KEY: primer_bind
<222> LOCATION: (1)..(26)

<400> SEQUENCE: 26
cggaattcag caacatcaag gagaac                                     26

<210> SEQ ID NO 27
<211> LENGTH: 28
<212> TYPE: DNA
<213> ORGANISM: Artificial Sequence
<220> FEATURE:
<223> OTHER INFORMATION: SiteO-HindIII-R
<220> FEATURE:
<221> NAME/KEY: primer_bind
<222> LOCATION: (1)..(28)

<400> SEQUENCE: 27
cccaagcttc ttgttcacga tgggcagc                                   28

<210> SEQ ID NO 28
<211> LENGTH: 27
<212> TYPE: DNA
<213> ORGANISM: Artificial Sequence
<220> FEATURE:
<223> OTHER INFORMATION: HBc148-NcoI-F
<220> FEATURE:
<221> NAME/KEY: primer_bind
<222> LOCATION: (1)..(27)

<400> SEQUENCE: 28
ccgccatgga cattgaccct tataaag                                    27

<210> SEQ ID NO 29
<211> LENGTH: 30
<212> TYPE: DNA
<213> ORGANISM: Artificial Sequence
<220> FEATURE:
<223> OTHER INFORMATION: HBc148-XhoI-R
```

```
<220> FEATURE:
<221> NAME/KEY: primer_bind
<222> LOCATION: (1)..(30)

<400> SEQUENCE: 29
catgctcgag aacagtagtt tccggaagtg                                        30

<210> SEQ ID NO 30
<211> LENGTH: 22
<212> TYPE: DNA
<213> ORGANISM: Artificial Sequence
<220> FEATURE:
<223> OTHER INFORMATION: CpG

<400> SEQUENCE: 30
tcgtcgtttt cggcgcgcgc cg                                                22
```

VACCINE COMPOSITION COMPRISING HEPATITIS B VIRUS LIKE PARTICLE AS ADJUVANT

CROSS-REFERENCE TO RELATED APPLICATIONS

The present application is a U.S. national stage application, filed under 35 U.S.C. § 371, of PCT/CN2017/112350 filed Nov. 22, 2017, which claims the priority of U.S. Provisional Application Ser. No. 62/425,079 filed on Nov. 22, 2016 which is herein incorporated by reference in their entirety.

SEQUENCE LISTING

The instant application contains a Sequence Listing which has been submitted electronically in ASCII format and is hereby incorporated by reference in its entirety. Said ASCII copy, created on May 20, 2019, is named 068293-644N01US_sequence listing_20190520.txt and is 13 KB in size.

BACKGROUND

1. Technical Field

The present disclosure relates to vaccine compositions and methods of enhancing immunogenicity and improving an immune response of antigens.

2. Description of Associated Art

The global market of vaccine adjuvants is expected to reach USD 769.4 Million by 2021 from USD 467.0 Million in 2016. The major factors driving the growth of this market are high prevalence of infectious and zoonotic diseases, increasing focus on immunization programs by various government agencies, and growing focus on improved and long-lasting immunization against existing and emerging diseases.

In recent years, there has been widespread concern about vaccines delivered through mucosal surfaces because mucosal surfaces are the port of entry of the majority of the infectious agents, and it is important to the health of an animal to have developed a strong protective antibody and cell-mediated immune response at the port of entry. A mucosal vaccine can be done with an adjuvant and delivery system that would adsorb the vaccine antigens onto the mucosal surface of the oral cavity, gut, nose, rectum, or vagina, and then, following absorption, be brought in contact with mucosa-associated lymphoid tissue. Hence, mucosal vaccines are advantageous to provide the benefit of effectively inducing the systemic immunity (production of IgG antibody) and the mucosal immunity (production of secretory IgA antibody), and they are also cheap, easily administered and suitable for mass vaccinations.

As one of the commonly used adjuvants in immunology, aluminum salts have been used in vaccines since the 1930s. However, even widely used in the world, aluminum salts are comparatively weak and only work in certain diseases.

Therefore, there is a need for a mucosal vaccine having an adjuvant capable of penetrating the mucosal epithelia and inducing an immune response that is both protective and long-lasting.

SUMMARY

In view of the foregoing, the present disclosure provides a vaccine composition comprising an antigen and an adjuvant, wherein the adjuvant is a recombinant hepatitis B core virus-like particle (HBc VLP), hereinafter also briefly called "HBc."

The recombinant HBc VLP may comprise an amino acid sequence at least 80% identical to the amino acid sequence of SEQ ID NO: 1 (MDIDPYKEFGATVELLSFLPSDFFPS-VRDLLDTASALYREALESPEHCSPHHTAL RQAILC-WGELMTLATWVGNNLEDPASRDLVVNYVNTNM-GLKIRQLLWFHISCL TFGRETVLEYLVSFGVWIRTP-PAYRPPNAPILSTLPETTV) and has the same function as SEQ ID NO: 1. In an embodiment of the present disclosure, the adjuvant is a HBc VLP consisting of the amino acid sequence of SEQ ID NO: 1.

In an embodiment of the present disclosure, the antigen may be an antigen derived from an infectious disease. In another embodiment of the present disclosure, the antigen is derived from one selected from the group consisting of human immunodeficiency virus, varicella zoster virus, herpes simplex virus type 1, herpes simplex virus type 2, human cytomegalo virus, dengue virus, hepatitis A, B, C or E virus, respiratory syncytial virus (RSV), severe acute respiratory syndrome virus (SARS virus), human papilloma virus, influenza virus, *Haemophilus influenzae* type b (Hib), meningitis virus, *Salmonella, Neisseria, Borrelia, Chlamydia, Bordetella*, enterotoxic *E. coli, Campylobacter, Streptococcus, Moraxella, Mycoplasma, Mycobacteria, Haemophilus*, Plasmodium or Toxoplasma, and Stanworth decapeptide.

According to a further aspect of the present disclosure, the present disclosure provides a method of vaccinating a subject, comprising administering the vaccine composition described above to a mucosal surface of the subject.

In another embodiment of the present disclosure, the mucosal surface may be selected from the group consisting of respiratory, gastrointestinal, vaginal, nasal, rectal and oral mucosa.

The present disclosure provides a recombinant HBc VLP. Also, the present disclosure provides a vaccine composition comprising an antigen from an infectious agent and an adjuvant-effective amount of the recombinant HBc VLP as an adjuvant. The vaccine composition of the present disclosure can induce antibody responses specific for the antigen in a subject and protect the subject from the infectious agent without causing an adverse effect. As such, the adjuvant, the vaccine composition and the method of achieving immunity of the present disclosure are relatively easy in mass production and more helpful in increasing the specificity of antibody identification and avoiding unnecessary reactions such as allergy.

BRIEF DESCRIPTION OF THE DRAWINGS

The present disclosure can be more fully understood by reading the following detailed description of the embodiments, with reference made to the accompanying drawings, wherein:

FIGS. 1A-1I are results of SDS-PAGE analysis of HRØ24, HRØ, HRØ-3Ø recombinant proteins, and HBc. FIGS. 1A, 1C, 1E, and 1G show Coomassie blue staining of purified HRØ24, HRØ, HRØ-3Ø recombinant proteins, and HBc, respectively; FIGS. 1B, 1D, and 1F show western blotting of purified HRØ24, HRØ, and HRØ-3Ø recombinant proteins using anti-His antibody, respectively; FIG. 1H shows western blotting of purified HBc using rabbit polyclonal anti-HBc antibody; and FIG. 1I shows western blotting of purified HBc and HRØ24 recombinant proteins using mouse monoclonal anti-RSV antibody, respectively.

FIG. 3A shows that mice in each group are immunized 4 times with vaccine candidates on week 0, 3, 6, and 9, and received RSV challenge on week 12; and FIG. 3B shows that mice in each group are immunized 3 times with vaccine candidates on week 0, 3, and 6, and received RSV challenge on week 9. A group immunized with formalin-fixed RSV (FIRSV) intramuscularly (i.m) before RSV challenge is also included. Mouse serum, BALF and spleens are collected from separate groups with identical dosing regimen 2 days before RSV challenge.

FIGS. 4A-4F show HRØ24- and FIRSV-specific antibody responses in mice received 4 doses of intranasal administration of HRØ24 mixed with or without HBc VLPs. Mouse serum of each group is collected 2 days before RSV challenge. FIGS. 4A-4C show HRØ24-specific total IgG, IgG1, and IgG2a responses measured from the serum, respectively; and FIGS. 4D-4F show FIRSV-specific total IgG, IgG1, and IgG2a responses measured from the serum, respectively.

FIGS. 5A-5K show HRØ24- and FIRSV-specific antibody responses and splenocytes re-stimulation in mice received 4 doses of intranasal administration of HRØ24 and HBc VLPs mixture with or without CpG. Mouse serum, BALF, and spleens of each group are collected 2 days before RSV challenge. FIGS. 5A-5D show HRØ24-specific total IgG, IgG1, and IgG2a responses and a ratio of IgG2a/IgG1 measured from the serum, respectively; FIGS. 5E-5H show FIRSV-specific total IgG, IgG1, and IgG2a responses and a ratio of IgG2a/IgG1 measured from the serum, respectively; FIGS. 5I and 5J show HRØ24- and FIRSV-specific secretory IgA (sIgA) responses detected from the BALF, respectively; and FIG. 5K shows the level of IFN-γ detected in the antigen re-stimulation experiments.

FIGS. 6A-6H show RSV F protein site Ø- and site II-specific antibody responses in mice received 4 doses of intranasal administration of HRØ24 and HBc VLPs mixture with or without CpG. Mouse serum of each group is collected 2 days before RSV challenge. FIGS. 6A-6D show site Ø-specific total IgG, IgG1, and IgG2a responses and a ratio of IgG2a/IgG1 measured from the serum, respectively; and FIGS. 6E-6H show site II-specific total IgG, IgG1, and IgG2a responses and a ratio of IgG2a/IgG1 measured from the serum, respectively.

FIGS. 7A, 7B, 7C, and 7E show HRØ24-specific total IgG, IgG1, IgG2a and IgA responses measured from the serum, respectively; and FIG. 7D shows HRØ24-specific sIgA response detected from the BALF.

DETAILED DESCRIPTION OF THE EMBODIMENTS

Figure 2:
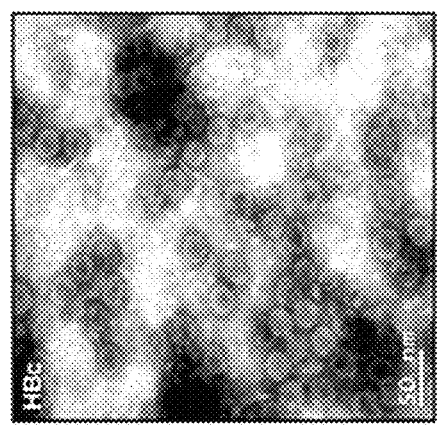
FIG. 2 shows the transmission electron microscopy (TEM) image of purified HBc.

The following examples are used to exemplify the present disclosure. A person of ordinary skills in the art can conceive the other advantages of the present disclosure, based on the specification of the present disclosure. The present disclosure can also be implemented or applied as described in different specific examples. It is possible to modify and/or alter the above examples for carrying out this disclosure without contravening its spirit and scope, for different aspects and applications.

As used herein, the singular forms "a," "an" and "the" include plural referents unless the context clearly dictates otherwise. Thus, for example, reference to "an antigen" includes mixtures of antigens; reference to "a pharmaceutically acceptable carrier" includes mixtures of two or more such carriers, and the like. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A (alone)," and "B (alone)."

The present disclosure provides a vaccine composition comprising an antigen and an adjuvant, wherein the adjuvant is a recombinant HBc VLP.

As used herein, the term "virus-like particle" (VLP) refers to a structure resembling a virus but is non-infectious because it is devoid of the viral genome. The term "non-infectious," as used herein, refers to being incapable of entering the host cell. Typically, virus-like particles are incapable of replication and devoid of pathogenicity, since they lack all or a portion of the viral genome, in particular the replicative and infectious components of the viral genome. The virus-like particles may be a viral capsid such as the viral capsid of the corresponding virus coated with a lipid membrane known as the viral envelope. The terms "viral capsid" or "capsid" refer to a macromolecular assembly composed of viral protein subunits. Also, virus-like particles can often be produced in large quantities by heterologous expression and can be easily purified.

VLPs can form spontaneously upon recombinant expression of the protein in an appropriate expression system. Methods for producing particular VLPs are known in the art. The presence of VLPs can be detected using conventional techniques known in the art, such as by electron microscopy, X-ray crystallography, and the like.

In an embodiment of the present disclosure, the adjuvant may be a recombinant hepatitis B core antigen (HBcAg). In another embodiment of the present disclosure, the adjuvant may be a recombinant HBcAg having an amino acid sequence at least 80% identical to the amino acid sequence of SEQ ID NO: 1 and having the same function as SEQ ID NO: 1. In yet another embodiment of the present disclosure, the recombinant HBcAg comprises an amino acid sequence at least about 80%, 85%, 90%, 95%, 96%, 97%, 98%, or 99% identical to the amino acid sequence of SEQ ID NO: 1.

As used herein, the term "sequence identity" or, for example, comprising a "sequence 80% identical to," as used herein, refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 80%, 85%, 90%, 95%, 97%, 98%, 99% or 100% sequence identity to any of the reference sequences described herein (see, e.g., Sequence Listing), typically where the polypeptide variant maintains at least one biological activity or function of the reference polypeptide.

In an embodiment of the present disclosure, the adjuvant is a recombinant HBcAg consisting of the amino acid sequence of SEQ ID NO: 1, hereinafter also called "HBcAg148," which has been confirmed to form a virus-like particle.

The present disclosure provides an adjuvant composition comprising HBcAg148 virus-like particles, wherein the HBcAg148 virus-like particles are inert, with empty capsids, and formed by the self-assembly of capsid proteins from hepatitis B virus (HBV). HBV is a small, enveloped virus with a circular, partially double-stranded DNA genome. It is a major cause of infectious liver disease throughout the world. HBV infection affects approximately 2 billion people in the world, and HBV infection of adults is usually transient. HBcAg is an antigen that can be found on the surface of the nucleocapsid core, i.e., the inner most layer of HBV. HBcAg148 VLPs are non-infectious because they assemble without incorporating genetic materials.

In an embodiment of the present disclosure, the antigen is derived from an infectious disease, including, but not limited to, human immunodeficiency virus, varicella zoster virus, herpes simplex virus type 1, herpes simplex virus type 2, human cytomegalo virus, dengue virus, hepatitis A, B, C or E virus, RSV, SARS virus, human papilloma virus, influenza virus, Hib, meningitis virus, *Salmonella, Neisseria, Borrelia, Chlamydia, Bordetella*, enterotoxic *E. coli, Campylobacter, Streptococcus, Moraxella, Mycoplasma, Mycobacteria, Haemophilus*, Plasmodium or Toxoplasma, and Stanworth decapeptide.

The above antigen derived from an infectious disease refers to any substances targeted by the immune response developed in a test organism. The above antigen derived from an infectious disease may also be the target of the immune response (e.g., aging of immunocompetent cells, cytokine production, and antibody production) at the contact with the immunocompetent cell.

In an embodiment of the present disclosure, the antigen may be derived from RSV. As descried herein, RSV has been recognized as the most common cause of lower respiratory tract infections in infants and young children. RSV has three surface glycoproteins, i.e., small hydrophobic (SH), attachment (G) and fusion (F), encoded by three consecutive genes (SH-G-F). The major target antigens of RSV vaccine development are RSV F and G as these are each capable of generating neutralizing antibodies as well as T cell responses. F is particularly attractive due to its considerable conservation among RSV isolates. Historically, there were two known major antigenic sites found on both the prefusion and postfusion conformations of RSV F associated with neutralizing (NT) activity. They were initially defined by binding to the murine monoclonal antibodies (mAbs) 1129 (site II) (Beeler, J. A. et al., 1989; Arbiza, J., et al., 1992) and 101F (site IV) (Wu, S. J., et al., 2007). Site II is known as the target for palivizumab which can reduce severe RSV disease in high-risk infants. McLellan et al. (McLellan, J. S., et al., 2013) isolated a mouse antibody, 5C4, which neutralized RSV potently but showed no binding to postfusion F protein. 5C4 shares these properties with two other antibodies isolated from immortalized PBMCs, D25 and AM22, which have been shown to neutralize RSV with 100 folds greater potency than palivizumab (McLellan, J. S., et al., 2013). D25 and AM22 target site Ø, a metastable antigenic site located on the surface of the prefusion RSV F trimer (Spits, H., et al., 2010; Beaumont, T., et al., 2012). The prefusion and postfusion crystal structures of F protein suggest that while sites II and IV are found on both structures, site Ø appears to be specific for the prefusion form (McLellan, J. S., et al., 2013).

The fusion peptide region of RSV F is located at the N terminus of the F1 subunit (Collins, P. L., et al., 1996) while the transmembrane segment contains two regions of 4,3-hydrophobic heptad repeats (HR), a sequence motif suggestive of coiled-coil structures (Chambers, P., et al., 1990; Singh, M., et al., 1999). These regions are denoted as HRN and HRC, respectively, and are separated by an intervening domain of about 270 amino acids. HRN and HRC form a trimeric hairpin-like structure, with the HRC regions packing in an antiparallel manner against the inner coiled-coil formed by HRN regions (Baker, K. A., et al., 1999).

In an embodiment of the present disclosure, the antigen is a recombinant RSV F protein comprising an HRN region, an HRC region, and at least one antigenic site selected from the group consisting of site Ø, site II, and site IV. In another embodiment of the present disclosure, the antigen may be represented by one of SEQ ID NOs: 2 to 4.

In an embodiment, the vaccine composition may be used to induce an immune response to infectious agents, such as RSV, in a subject. Thus, in several embodiments, the vaccine composition comprising the recombinant RSV F protein as an antigen in a therapeutically effective amount can be administered to a subject to elicit an immune response to RSV.

In another embodiment of the present disclosure, the vaccine composition comprising the recombinant RSV F protein as an antigen in a therapeutically effective amount is administered to a subject in need under conditions sufficient to prevent or ameliorate an RSV infection in the subject. The vaccine composition is administered in an amount sufficient to elicit an immune response against an RSV antigen, such as RSV F protein, in the subject. In an embodiment of the present disclosure, the vaccine composition is suitable for mucosal vaccination and may be administered orally, nasally, rectally, or vaginally to the subject.

In an embodiment of the present disclosure, the adjuvant in the vaccine composition is present in an adjuvant-effective amount of 0.1 µg to 1000 µg. In another embodiment of the present disclosure, the vaccine composition comprises a mixture of the antigen and the adjuvant at a weight ratio of 10:1 to 1:10. In yet another embodiment of the present disclosure, the antigen and the adjuvant comprised in the vaccine composition is at a weight ratio of 5:1 to 1:5.

In an embodiment of the present disclosure, the HBc VLP in the vaccine composition is used as the sole adjuvant that effectively potentiates the immune responses to an antigen and/or modulates it towards the desired immune responses. In another embodiment of the present disclosure, the vaccine composition may comprise an additional adjuvant. The additional adjuvants useful for the present disclosure may include, but not limited to, a CpG oligonucleotide.

In an embodiment of the present disclosure, the vaccine composition may further comprise a pharmaceutically acceptable carrier. As used herein, the "pharmaceutically acceptable carrier" includes any and all solvents, dispersion media, antibacterial and antifungal agents, isotonic and absorption delaying agents and the like which may be appropriate for administration of the vaccine composition of the present disclosure. The pharmaceutically acceptable carrier useful for the present disclosure may include, but not limited to, a preservative, a suspending agent, a tackifier, an isotonicity agent, a buffering agent, and a humectant.

The present disclosure further provides a method for preparing a vaccine composition, comprising providing an adjuvant composition comprising an HBcAg148 VLP and a pharmaceutically acceptable carrier, and combining the adjuvant composition with a recombinant RSV F protein as an antigen. In an embodiment of the present disclosure, the HBcAg148 VLP consists of the amino acid sequence of SEQ ID NO: 1.

According to a further aspect of the present disclosure, the present disclosure provides a nucleic acid molecule encoding the HBcAg148 VLP described above. In an embodiment of the present disclosure, the nucleic acid molecule is codon optimized for expression in a prokaryotic cell. In another embodiment, the prokaryotic cell is an *Escherichia coli* cell. In yet another embodiment, the nucleic acid molecule comprises a nucleic acid sequence at least about 80%, 85%, 90%, 95%, 96%, 97%, 98%, or 99% identical to the nucleic acid sequence of SEQ ID NO: 5 (ATGGACATTGACCCT-TATAAAGAATTTGGAGCTACTGTGGAGTTACTCTC-GTT TTTGCCTTCTGACTTCTTTCCTTCCGTCAGA-GATCTTCTAGACACCGCCTCAG CTCTGTATCGA-GAAGCCTTAGAGTCTCCTGAGCATTGCTCACCT-CACCATACT GCACTCAGGCAAGCCATTCTCTGCT-GGGGGGAATTGATGACTCTAGCTACCT GGGTGG-GTAATAATTTGGAAGATCCAGCATCCAGGGATCT-AGTAGTCAATTAT GTTAATACTAACATGGGTTTAAA-GATCAGGCAACTATTGTGGTTTCATATATCT TGCCT-TACTTTTGGAAGAGAGACTGTACTTGAATATTTGG-TCTCTTTCGGAGT GTGGATTCGCACTCCTCCAGCC-TATAGACCACCAAATGCCCCTATCTTATCAA CACT-TCCGGAAACTACTGTT).

In an embodiment of the present disclosure, the nucleic acid molecule is codon optimized for expression in a eukaryotic cell. In another embodiment, the eukaryotic cell is a yeast cell or a mammalian cell. In yet another embodiment, the mammalian cell is a human cell.

The present disclosure further provides a method of inducing a mucosal immune response and a systemic immune response by the vaccine composition described above. The vaccine composition is administered to a subject in need thereof, thereby inducing a mucosal immune response and a systemic immune response in the subject, wherein the mucosal immune response is the production of antigen-specific IgA antibody, and the systemic immune response is the productions of antigen-specific IgG antibody and antigen-specific cell-mediated immune.

According to a further aspect of the present disclosure, the present disclosure provides a method of vaccinating a subject, comprising administering the vaccine composition described above to the subject. Vaccination methods comprise use of a vaccine composition to be administered by any conventional route known in the vaccine field, e.g., via a mucosal (e.g., ocular, intranasal, pulmonary, oral, gastric, intestinal, rectal, vaginal, or urinary tract) surface, via a parenteral (e.g., subcutaneous, intradermal, intramuscular, intravenous, or intraperitoneal) route, or topical administration (e.g., via a transdermal delivery system such as a patch).

In an embodiment of the present disclosure, the vaccine composition is administered to a mucosal surface of the subject. In another embodiment of the present disclosure, the mucosal surface may be selected from the group consisting of respiratory, gastrointestinal, vaginal, nasal, rectal and oral mucosa.

Many examples have been used to illustrate the present disclosure. The examples below should not be taken as a limit to the scope of the disclosure.

EXAMPLE

Example 1

Construction of Recombinant HBc VLP Expression Vector

Full length cDNA sequence of HBc protein with optimized codon for *Escherichia coli* (*E. coli*) expression was synthesized (Genomics BioSci & Tech). Using this sequence as the PCR template, nucleotides 1-444 of HBc (SEQ ID NO: 5) was amplified and then inserted into the NcoI-XhoI restriction sites of pET28a tagged with 6-His at the C-terminus to obtain a recombinant HBc VLP plasmid. The resulting plasmid was transformed into *E. coli* BL21 (DE3) competent cells for protein expression.

Example 2

Construction of Recombinant RSV Chimera F Protein Expression Vector

Full length cDNA sequence of RSV F protein with optimized codon for *Escherichia coli* (*E. coli*) expression was synthesized (Genomics BioSci & Tech). Using this sequence as the PCR template, four gene fragments of RSV F protein were amplified, including nucleotides 457-633 which contain HRN and site Ø (SEQ ID NO: 6), nucleotides 760-849 which contain site II (SEQ ID NO: 7), nucleotides 1264-1314 which contain site IV (SEQ ID NO: 8), and nucleotides 1426-1560 which contain the C-terminal α-helix (HRC) (SEQ ID NO: 9).

These four PCR amplicons were linked by overlapping PCR and connected by a glycine-rich linker, such as GSGS, GGGS, GGSG, SGSG and GG, to form a constructed gene (named HRØ24), which was then inserted into the NcoI-XhoI restriction sites of pET28b tagged with 6-His at the C-terminus to obtain an HRØ24 plasmid.

The process of construction of HRØ, HRØ-3Ø and HBc plasmids were similar to that of the HRØ24 plasmid, except for the differences as follows.

For the construction of HRØ plasmids, two gene fragments of RSV F protein represented by SEQ ID NOs: 6 and 9 were amplified. These two PCR amplicons were then inserted into the NcoI/BamHI and EcoRI/XhoI restriction sites of pET28a tagged with 6-His at the C-terminus and connected by a glycine-rich linker to obtain an HRØ plasmid.

For the construction of HRØ-3Ø plasmids, two gene fragments of RSV F protein represented by SEQ ID NOs: 6 and 9 were amplified. Further, three site Ø fragments containing NheI/BamHI, BamHI/EcoRI, or EcoRI/HindIII restriction sites were created by PCR. These five PCR amplicons were then inserted into the NcoI NheI/BamHI/EcoRI/HindIII/XhoI restriction sites of pET28a tagged with 6-His at the C-terminus and connected by a glycine-rich linker to obtain an HRØ-3Ø plasmid.

The above resulting plasmids were transformed into *E. coli* BL21 (DE3) competent cells for protein expression.

The primers used for PCR in Examples 1 and 2 were represented by SEQ ID NOs: 10 to 29, shown in Table 1 below.

TABLE 1

| Primer sequences | |
|---|---|
| Primer | Sequence |
| HRN-NcoI-F | 5'-CCG CCA TGG CCG TGT CTA AGG TGC TGC-3' (SEQ ID NO. 10) |
| HRC-XhoI-R | 5'-CAT GCT CGA GCT TGC CGG CGT TCA CAT TG-3' (SEQ ID NO. 11) |
| HRN-A1-F | 5'-CAT CGT GAA CAA GCA GAG CGG TTC TGG TTC TAA CAG CGA GCT GCT GAG-3' (SEQ ID NO. 12) |
| HRN-A1-R | 5'-CTC AGC AGC TCG CTG TTA GAA CCA GAA CCG CTC TGC TTG TTC ACG ATG-3' (SEQ ID NO. 13) |
| A1-A2-F | 5'-GCA GAT CGT GCG GCA GGG TGG TGG TTC TTG CAC CGC CAG CAA C-3' (SEQ ID NO. 14) |
| A1-A2-R | 5'-GTT GCT GGC GGT GCA AGA ACC ACC ACC CTG CCG CAC GAT CTG C-3' (SEQ ID NO. 15) |
| A2-HRC-F | 5'-AGA CCT TCA GCA CGG CGT GGT TCT GTA ACT TCT ACG ACC CCT GG-3' (SEQ ID NO. 16) |
| A2-HRC-R | 5'-CCA GGG GGT CGT AGA AGT TAC AGA ACC ACC GCC GTT GCT GAA GGT CT-3' (SEQ ID NO. 17) |
| Site Ø-N-F | 5'-GCC GGA TCC AGC AAC ATC AAG GAG AAC AAG TGC AAC GCC GCC AAG AAC TAC ATC GAC AA-3' (SEQ ID NO. 18) |
| Site Ø-C-R | 5'-GCC AAG CTT CTT GTT CAC GAT GGG CAG CAG CTG CTT GTC GAT GTA GTT CTT GGC GGC GTT-3' (SEQ ID NO. 19) |
| HRN-BamHI-R | 5'-GCC GGA TCC AGA ACC AGA ACC GCT CTG CTT G-3' (SEQ ID NO. 20) |
| HRC-EcoRI-F | 5'-CGG AAT TCG TGG TTC TGT AAC TTC TAC GAC-3' (SEQ ID NO. 21) |
| Site Ø-NheI-F | 5'-CTA GCT AGC AGC AAC ATC AAG GAG AAC-3' (SEQ ID NO. 22) |
| Site Ø-BamHI-R | 5'-GCC GGA TCC GCC TCC CTT GTT CAC GAT GGG CAG C-3' (SEQ ID NO. 23) |
| Site Ø-BamHI-F | 5'-GCC GGA TCC AGC AAC ATC AAG GAG AAC-3' (SEQ ID NO. 24) |
| Site Ø-EcoRI-R | 5'-CGG AAT TCG CCT CCC TTG TTC ACG ATG GGC AGC-3' (SEQ ID NO. 25) |
| Site Ø-EcoRI-F | 5'-CGG AAT TCA GCA ACA TCA AGG AGA AC-3' (SEQ ID NO. 26) |
| Site Ø-HindIII-R | 5'-CCC AAG CTT CTT GTT CAC GAT GGG CAG C-3' (SEQ ID NO. 27) |

TABLE 1-continued

Primer sequences

| Primer | Sequence |
|---|---|
| HBc148-NcoI-F | 5'-CCG CCA TGG ACA TTG ACC CTT ATA AAG-3' (SEQ ID NO. 28) |
| HBc148-XhoI-R | 5'-CAT GCT CGA GAA CAG TAG TTT CCG GAA GTG-3' (SEQ ID NO. 29) |

Example 3

Recombinant Protein Expression and Purification

The recombinant RSV F protein-6His and HBc-6His were expressed in the transformed E. coli BL21 (DE3) obtained from Examples 1 and 2, and purified using nickel affinity chromatography, respectively. Eluted (with 500 mM imidazole, 50 mM $NaH_2PO_4$, 300 mM NaCl, pH 8.0) protein was buffer exchanged by gradient dialyzing 1 volume of sample against 200 volumes of dialyzing buffer (from 350 mM, 150 mM to 0 mM imidazole in 1×PBS) for 12 h in each step. The dialyzed protein-6His was concentrated using a centrifugal concentrator (10,000 MWCO, Sartorius) to reach a concentration about 1 mg/mL. Molecule size and purity of the protein were determined by SDS-PAGE.

A band of identical mobility was detected by immunoblotting using antibodies directed against His tag, and the results were shown in FIGS. 1B, 1D, and 1F. A band of identical mobility was detected by immunoblotting using antibodies directed against HBc and RSV, and the results were shown in FIGS. 1H and 1I, respectively. Densitometric scanning of Coomassie blue stained gels revealed that the purified proteins HRØ24, HRØ, HRØ-3Ø and HBc amounted to more than 90% of the total protein (FIGS. 1A, 1C, 1E, and 1G), which was sufficiently pure for immunizations.

Example 4

Transmission Electron Microscope (TEM) Images of Recombinant HBc VLPs

8 μg of purified HBc VLPs in PBS were adsorbed onto a copper grid (300 mesh) for 3 min at room temperature. Then, the grids were dried gently using filter paper. After staining with 1% uranyl acetate aqueous solution for 30 seconds (s), the excess liquid was removed. The grids were examined with JEM-1400 electron microscope at 80 kV.

The HBc VLPs have been confirmed to form virus-like particles by TEM (FIG. 2).

Example 5

Animal Immunization

1. Preparation of RSV A2 Strain Stock

RSV A2 strain was obtained from ATCC. Propagation of the virus was performed in HEp-2 cells ATCC. Cells grown in 100 mm Petri dish (Thermo Scientific) up to 80% confluency were inoculated with RSV A2 at an m.o.i. (multiplicity of infection) of 0.2. Virus adsorption was carried out in serum free Dulbecco's Modified Eagle's medium (DMEM) in a $CO_2$ incubator at 37° C. After 2 hours, medium was replaced with DMEM supplemented with 2% fetal bovine serum, and the dishes were incubated for another 48-72 hours. Supernatants which contain the virus were separated from cell debris by centrifugation at 3,000 rpm for 10 min. Virus was then concentrated by a centrifugal concentrator (100,000 MWCO, Sartorius).

2. RSV Plaque Assay

RSV virus titer was determined by plaque assay. Confluent monolayer of HEp-2 cells in 12-well plates were washed with 1×PBS and then infected with RSV A2 virus at various dilutions ($10^{-3}$ to $10^{-7}$). After 2 hours of virus adsorption, supernatant was removed, and the cell monolayer was washed with 1×PBS, followed by overlaying with DMEM+ 2% fetal bovine serum+0.3% agarose. After 5 days incubation at 37° C. in a $CO_2$ incubator, cells were fixed with 10% formalin and stained with 0.05% crystal violet for plaque quantification.

3. Vaccine Administration and RSV Challenge

Figure 3A:
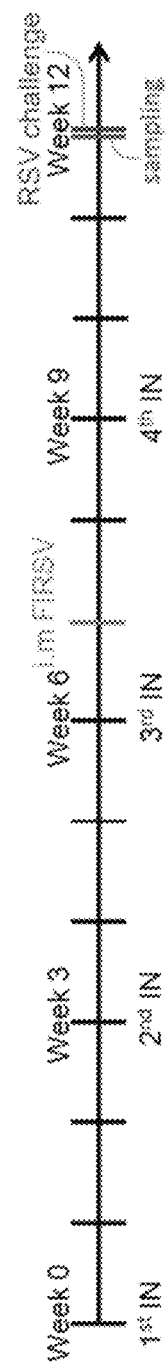
FIGS. 3A and 3B show the intranasal (IN) immunization schedule.
Figure 3B:
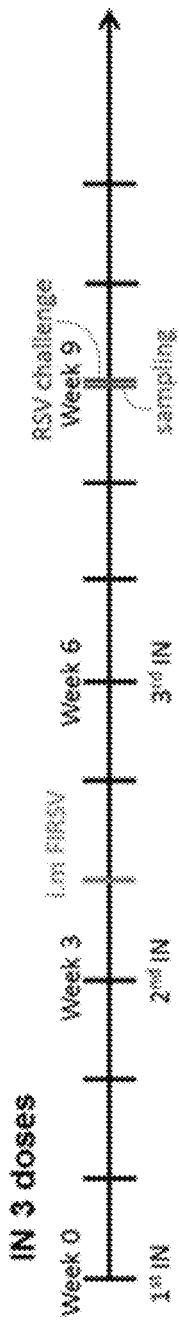

Pathogen-free C57BL/6J female mice (6-8 weeks old) were randomly divided into several groups and immunized by the intranasal (i.n) route with vaccine candidates on day 0, 21, 42 and 63 (FIG. 3A), or on day 0, 21 and 42 (FIG. 3B), and challenged with $1×10^6$ p.f.u. RSV on day 84 (FIG. 3A), or on day 63 (FIG. 3B). The vaccine candidates include: HRØ24; HBc VLPs+HRØ24; HBc VLPs+HRØ24+CpG (TCGTCGTTTTCGGCGCGCGCCG, SEQ ID NO. 30) (Genomics, Taiwan); HRØ; HBc VLPs+HRØ; HBc VLPs+ HRØ+CpG; HRØ-3Ø; HBc VLPs+HRØ-3Ø; and HBc VLPs+HRØ-3Ø+CpG. A naive control group, a group immunized only with HBc VLPs and a group immunized with $1×10^5$ p.f.u. formalin-fixed RSV (FIRSV) intramuscularly (i.m) were also included.

Mouse serum, bronchoalveolar lavage fluid (BALF) and spleens were collected from separate groups with identical dosing regimen 2 days before RSV challenge. For RSV challenge, the animals were anesthetized with 1.5% isoflurane and then infected by intranasal inoculation of $1×10^6$ p.f.u. RSV. After RSV challenge, body weights of the mice were monitored for 5 days. Finally, the mice were sacrificed and the individual lungs were collected for virus load and histopathology experiments.

Example 6

Evaluation of Antibody Response Elicited by Vaccine Candidates

Serum and BALF collected from the immunized mice as described in Example 5 were tested for antibody responses by enzyme-linked immunosorbent assay (ELISA). Briefly, a 96-well plate was coated with 50 μL of purified HRØ24 (10 μg/ml) overnight at 4° C. The plate was blocked with 2% BSA for 1 hour at 37° C., and incubated with serial dilutions of serum samples ($10^{-2}$ to $5.12×10^{-4}$) or BALF ($10^{-1}$ to $1.28×10^{-3}$) in assay diluent (1% BSA, 0.05% Tween 20 in 1×PBS) for 2 hours at room temperature. Dilution curve was drawn for each sample and endpoint titers were calculated as the reciprocal of the dilution producing an optical density that was 0.1 U greater than the background value (1/50 dilution of a pooled pre-immune serum or 1/5 dilution of a pooled naive BALF). IgG titers lower than 50 (negative samples) or secretory IgA (sIgA) titers lower than 5 were arbitrarily assigned as 50 or 5.

Referring to FIGS. 4A-4F which show the results of evaluating the immunogenicity of the vaccine candidates, groups of mice were immunized with 4 doses of i) HRØ24 (10 µg), ii) HRØ24 (50 µg), iii) HBc (10 µg)+HRØ24 (50 µg) or iv) HBc (10 µg) as a negative control by intranasal route. Final sera collected were analyzed by indirect ELISA for HRØ24-specific or FIRSV-specific IgG responses. The results indicated that intranasal immunization of HBc/HRØ24 mixture could generate significant higher HRØ24-specific total IgG, IgG1 and IgG2a (FIGS. 4A-4C). FIRSV-specific total IgG and IgG1 were also induced but not significantly higher (FIGS. 4D and 4E). These results confirmed that the HBc VLPs can enhance HRØ24-specific humoral responses.

Referring to FIGS. 5A-5J, in order to evaluate dose-response relationships of HBc VLPs, the groups of mice were immunized with 4 doses of i) HRØ24 (10 µg), ii) HBc VLPs (50 µg)+HRØ24 (10 µg), iii) HRØ24 (10 µg)+CpG (20 µg), iv) HBc VLPs (25 µg)+HRØ24 (10 µg)+CpG (20 µg) (annotated as HBc+HRØ24+CpG-1 in the figures), v) HBc VLPs (50 µg)+HRØ24 (10 µg)+CpG (20 µg) (annotated as HBc+HRØ24+CpG-2 in the figures) or vi) HBc VLPs (50 µg) intranasally. Sera and BALF were analyzed by indirect ELISA. FIGS. 5A-5C and 5I show that dosing with HBc VLPs/HRØ24 mixture can elicit significant higher serum HRØ24-specific total IgG, IgG1, IgG2a and lung HRØ24-specific sIgA. In addition, using CpG as an adjuvant did not enhance these humoral responses.

Figures 5I, 5J, 5K:
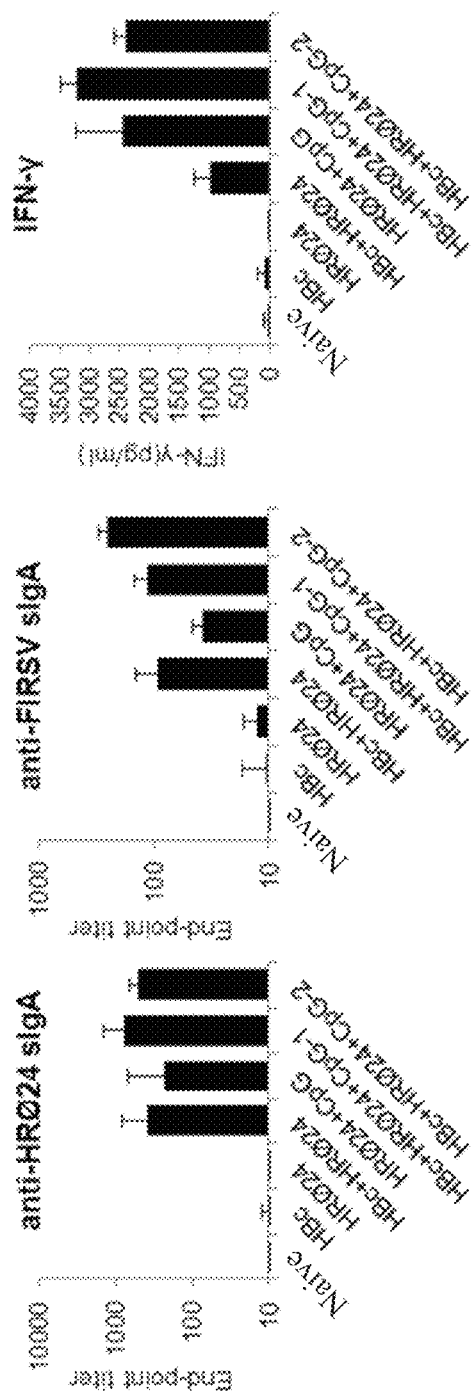
Figures 7A, 7B:
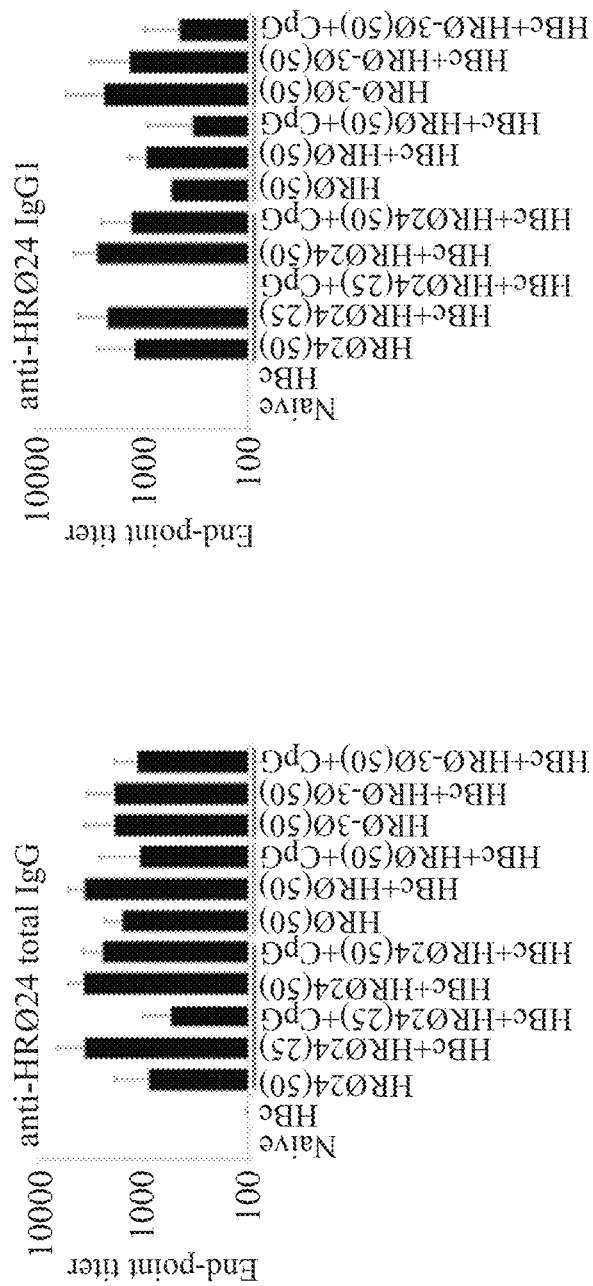
FIGS. 7A-7E show HRØ24-specific antibody responses in mice received 3 doses of intranasal administration of HRØ24, HRØ, or HRØ-3Ø mixed with or without HBc VLPs or CpG. Serum and BALF are collected from the mice 2 days before RSV challenge.
Figure 7D:
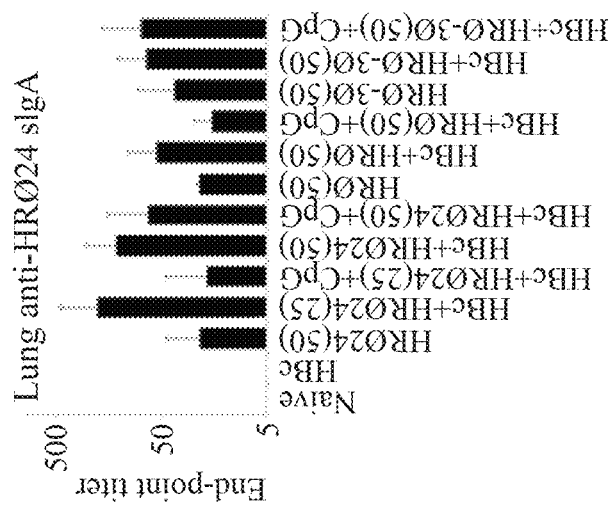
Figure 7C:
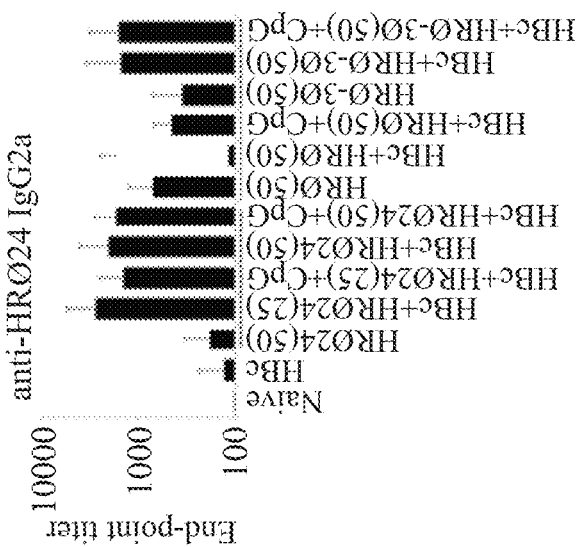
Figure 7E:
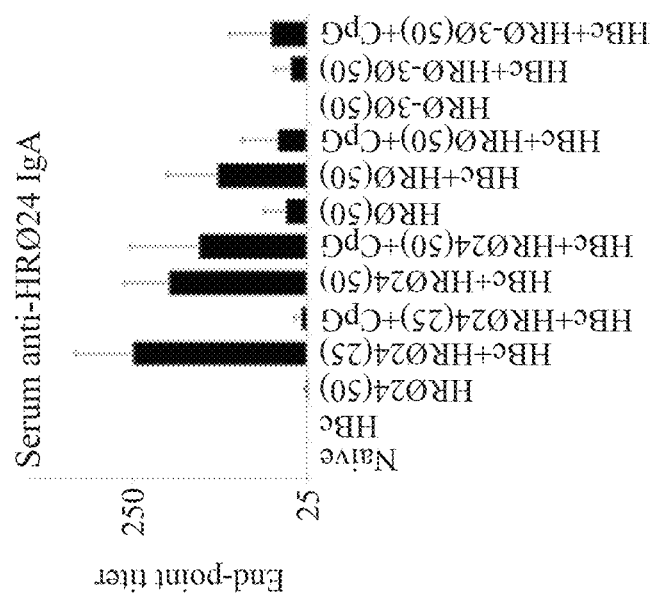

Since protective immunity against RSV required potent Th1 bias responses and IFN-γ production, the capacity of splenocytes from the immunized mice to respond to in vitro stimulation with HRØ24 recombinant protein was tested. T-cell proliferation from 48 h HRØ24-stimulated cultures was determined by mouse IFN-γ ELISA kit (BioLegend). Culture supernatants from these cells were analyzed for Ag-specific IFN-γ production. As shown in FIG. 5K, splenocytes from mice immunized with HRØ24 showed no IFN-γ secretion after HRØ24 stimulation. In contrast, splenocytes from mice immunized with HBc/HRØ24, HBc/HRØ24/CpG and HRØ24/CpG groups showed a significant higher level of IFN-γ secretion after HRØ24 stimulation. Notably, no IFN-γ secretion was noted in mice immunized with HBc or naive group.

Referring to FIGS. 6A-6H, in order to detect specific responses against RSV F protein antigenic sites, RSV F site Ø, II and IV peptides were used to coat ELISA plates (10 µg/mL). FIGS. 6A-6H showed that only mice receiving HBc/HRØ24 mixture can generate significant higher site Ø- and site II-specific total IgG, IgG1 and IgG2a. No site IV-specific IgG was detectable among all groups (data not shown).

Moreover, FIGS. 7A-7E showed HRØ24-specific antibody responses in mice received 3 doses of intranasal administration of HRØ24, HRØ, or HRØ-3Ø mixed with or without HBc VLPs or CpG. Mice in each group were immunized with 3 doses of i) HBc VLPs (25 µg), ii) HRØ24 (50 µg), iii) HBc VLPs (25 µg)+HRØ24 (25 µg), iv) HBc VLPs (25 µg)+HRØ24 (25 µg)+CpG (20 µg), v) HBc VLPs (25 µg)+HRØ24 (50 µg), vi) HBc VLPs (25 µg)+HRØ24 (50 µg)+CpG (20 µg), vii) HRØ (50 µg), viii) HBc VLPs (25 µg)+HRØ (50 µg), ix) HBc VLPs (25 µg)+HRØ (50 µg)+CpG (20 µg), x) HRØ-3Ø (50 µg), xi) HBc VLPs (25 µg)+HRØ-3Ø (50 µg), or xii) HBc VLPs (25 µg)+HRØ-3Ø (50 µg)+CpG (20 µg) intranasally. Sera and BALF were analyzed by indirect ELISA.

Referring to FIGS. 7A-7E, it was showed that by using HBc as an adjuvant, HRØ24, HRØ and HRØ-3Ø can elicit significant higher serum HRØ24-specific total IgG, IgG1, IgG2a, IgA and lung HRØ24-specific sIgA, in which the highest end-point titers were observed in the HBc/HRØ24 group. Moreover, by using the mixture of HBc and CpG as an adjuvant, HRØ24 can also elicit higher serum HRØ24-specific total IgG, IgG1, IgG2a, IgA and lung HRØ24-specific sIgA.

Example 7

Effects of Vaccine Candidates on Protecting Mice Against RSV Infection

To evaluate the efficacy when dosing the vaccine candidates 4 times, the immunized mice challenged with the live RSV A2 strain as described in Examples 5 and FIGS. 5A-6H were used.

1. Serum Neutralizing Titer After RSV Challenge

Figure 8:
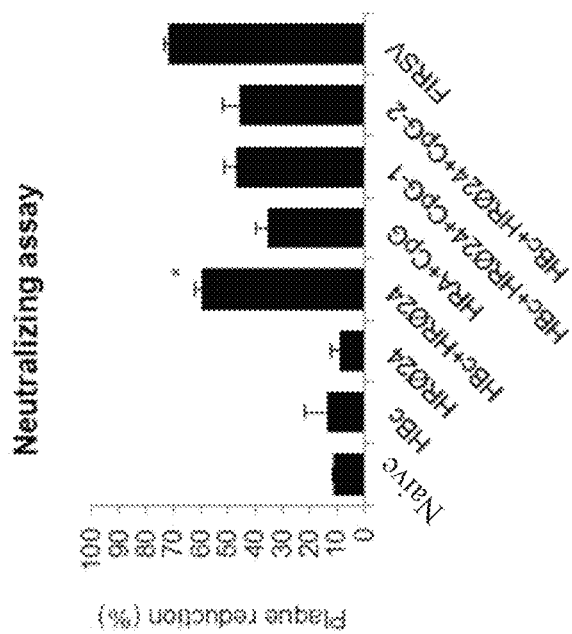
FIG. 8 shows the serum neutralizing titer. The serum of naive or vaccinated mice received 4 doses of intranasal administration is collected 2 days before RSV challenge, and tested for inhibition of RSV plaque formation.

Neutralizing antibody was an important functional component of immune responses induced by vaccination. FIG. 8 showed that serum from the HRØ24 group can reduce about 10% plaque formation, while serum from the HBc/HRØ24 group reduced about 25%, and the groups received CpG as an adjuvant can reduce about 17% to 35% plaque.

2. Mouse Body Weight Changes After RSV Challenge

Figure 9:
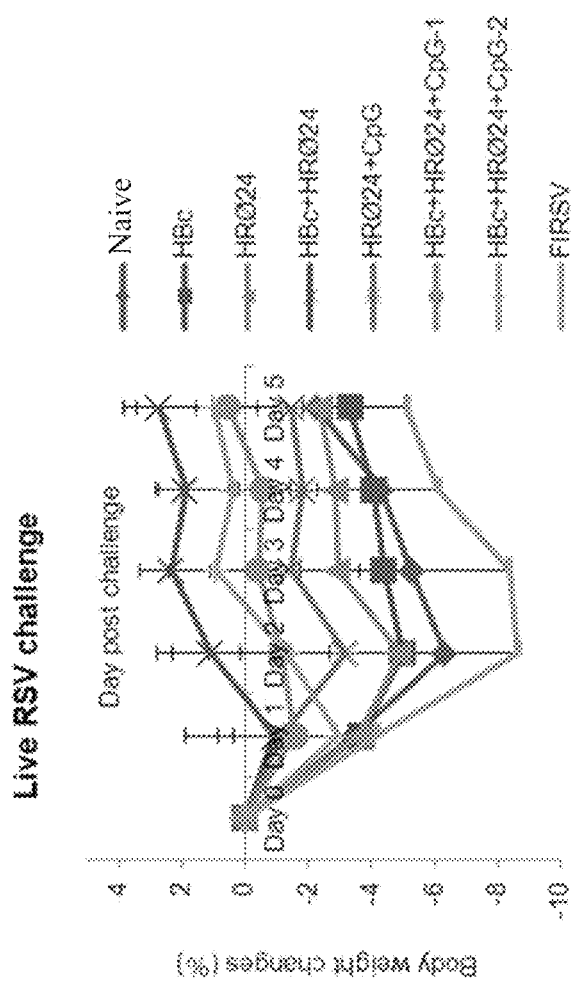
FIG. 9 shows mouse body weight changes after challenge. The body weight of naive or vaccinated mice received 4 doses of intranasal administration is monitored for 5 days after RSV challenge. Body weight changes are presented as the weight loss percentage compare to day 0.

Body weight change of mice following challenge infection was the most important indicator to assess vaccine protective efficacy. Referring to FIG. 9, mice received intramuscular injection of FIRSV showed the highest body weight loss (about 23%), whereas mice immunized with HBc/HRØ24 showed about 10% of body weight loss. Mice immunized with different dosages of HBc (0, 25, 50 µg), which were the groups of HRØ24+CpG, HBc+HRØ24+CpG-1, and HBc+HRØ24+CpG-2, showed about 8%, 4% and 0% body weight loss, respectively, at day 4 post challenge.

Therefore, the present disclosure provides a better protection to prevent mouse weight loss and an accelerated recovery from initial body weight loss following live RSV challenge. These are evidence that anti-viral immunity elicited by the antigen of the present application confers protection against live RSV A2 strain virus.

3. Lung Histopathology After RSV Challenge

Lung tissues were collected from individual mice at day 5 post challenge for histology analysis. For histological analysis, lung samples were fixed in 10% neutral buffered formalin for 24 hrs, embedded in paraffin blocks, sectioned into a thickness of 5 µm and stained with hematoxylin and eosin (H&E).

Figure 10:
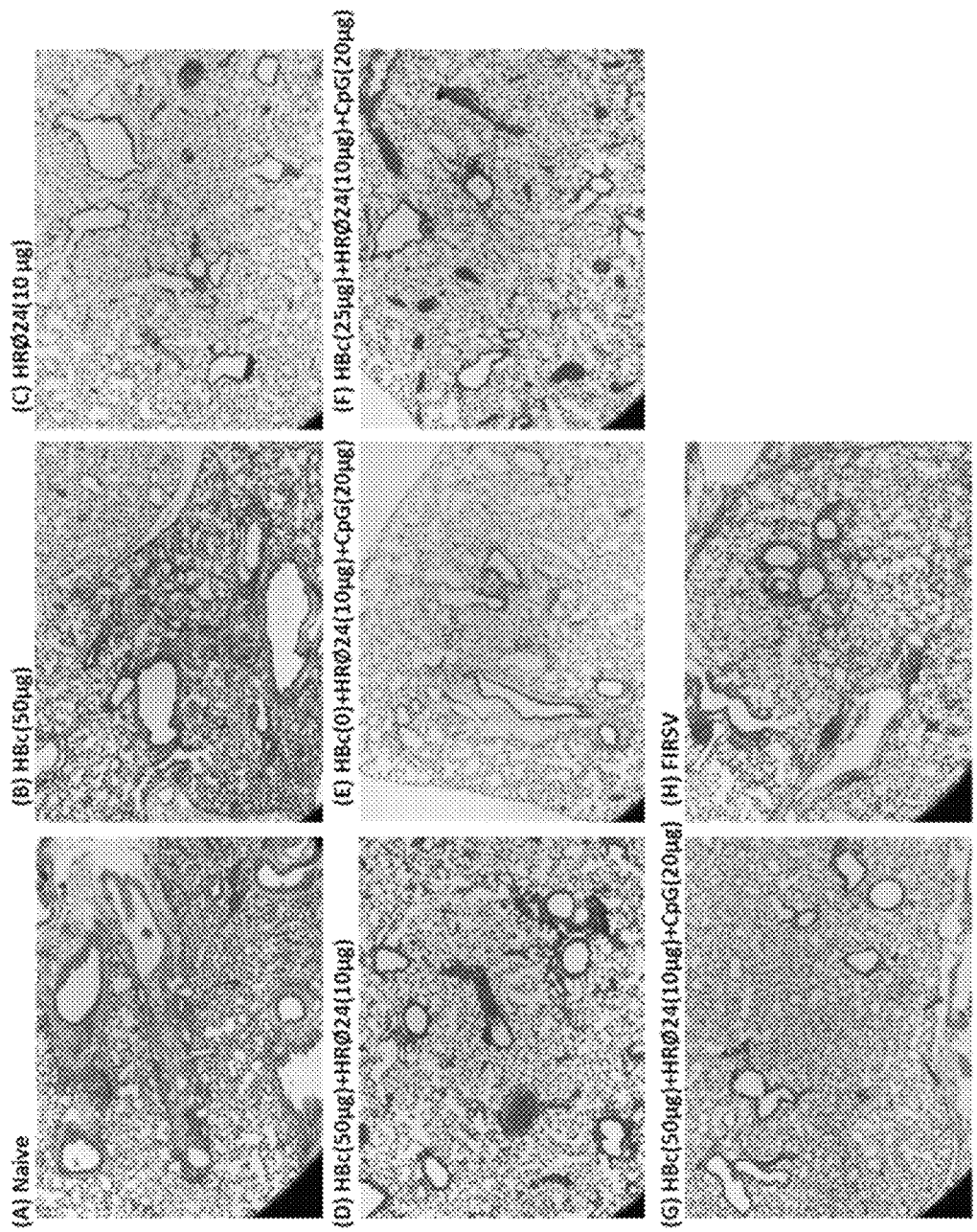
FIG. 10 shows lung histopathology. Lung tissues are collected from naive or vaccinated mice received 4 doses of intranasal administration at day 5 post RSV challenge for histology analysis.

Referring to FIG. 10, lung histopathological changes were observed in the naive group or vaccinated mice. FIRSV immunized mice showed a severe level of histopathology. When Lot 100 FIRSV vaccine was used in a clinical trial in the late 1960s, vaccinated children developed enhanced respiratory disease upon infection (Kim, H. W., et al., 1969). Also, the current study revealed that FIRSV induced prominent alveolitis and perivascusulitis in the lungs of RSV challenged mice. By contrast, as shown in FIG. 10, the groups of mice that received HBc/HRØ24 mixture with or without CpG displayed moderated lung pathology as evidenced by a certain degree of infiltrates around airways and alveolar. Further, significant lung histopathological changes were not observed in mice immunized with recombinant HRØ24 alone.

The present disclosure provides a purified HBcAg148 protein and a nucleic acid molecule encoding the HBcAg148 protein with an optimized codon for *E. coli* expression. The purified HBcAg148 protein has been confirmed to form virus-like particles by TEM. Further, the efficiency of HBcAg148 in enhancing the immune responses can be observed in vivo by dosing mice with the RSV vaccine candidate together with the adjuvant HBcAg148 intranasally. By the present disclosure, it is demonstrated that HBcAg148 could enhance serum total IgG, IgG1 and IgG2a responses against RSV and this adjuvant effect is similar to CpG motif.

Therefore, these results demonstrated that the vaccine composition of the present disclosure comprising the recombinant HBc VLP as an adjuvant can induce both systemic and mucosal antibody responses specific for the antigen. Mice immunized with the vaccine composition of the present disclosure showed protection against antigen without causing lung disease. Further, the vaccine composition of the present disclosure did not over-stimulate lymphocytes compared to FIRSV in a mouse model and offer as a potential safe RSV vaccine candidate.

The present disclosure has been described using exemplary embodiments in detail in the above. However, it is to be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

What is claimed is:

1. A vaccine composition comprising an antigen and an adjuvant, wherein the adjuvant is a hepatitis B core virus-like particle (HBc VLP) having an amino acid sequence at least 80% identical to an amino acid sequence of SEQ ID NO: 1 and having the same function as SEQ ID NO: 1, and wherein the antigen is derived from respiratory syncytial virus (RSV).

2. The vaccine composition of claim 1, wherein the adjuvant is the HBc VLP consisting of the amino acid sequence of SEQ ID NO: 1.

3. The vaccine composition of claim 1, wherein the antigen is a recombinant RSV F protein represented by one of SEQ ID NOs: 2 to 4.

4. The vaccine composition of claim 1, wherein the adjuvant is present in an adjuvant-effective amount of 0.1 µg to 1000 µg.

5. The vaccine composition of claim 1, having a weight ratio of the antigen to the adjuvant from 10:1 to 1:10.

6. The vaccine composition of claim 5, wherein the weight ratio of the antigen to the adjuvant is from 5:1 to 1:5.

7. The vaccine composition of claim 1, being suitable for mucosal vaccination.

8. The vaccine composition of claim 1, being suitable for oral, nasal, rectal, or vaginal application.

9. The vaccine composition of claim 1, inducing a mucosal immune response and a systemic immune response, wherein the mucosal immune response is antigen-specific secretory IgA antibody production, and the systemic immune response is antigen-specific IgG antibody production and antigen-specific cell-mediated immune production.

10. A method of vaccinating a subject, comprising administering the vaccine composition of claim 1 to a mucosal surface of the subject.

11. The method of claim 10, wherein the mucosal surface is selected from the group consisting of respiratory, gastrointestinal, vaginal, nasal, rectal and oral mucosa.

12. The method of claim 10, wherein the subject is human or animal.

* * * * *